United States Patent [19]

Dodrill

[11] Patent Number: 5,283,033
[45] Date of Patent: Feb. 1, 1994

[54] PROCESS FOR STERILIZING THE CONTENTS OF A SEALED DEFORMABLE PACKAGE

[75] Inventor: Robert K. Dodrill, Wheaton, Ill.

[73] Assignee: Advanced Retort Systems, Inc., Addison, Ill.

[21] Appl. No.: 800,326

[22] Filed: Nov. 29, 1991

[51] Int. Cl.$^5$ ............................................. A61L 2/00
[52] U.S. Cl. ..................................... 422/21; 422/25; 426/407
[58] Field of Search .................... 422/21, 25; 426/401, 426/407, 412, 232; 99/359

[56] References Cited

U.S. PATENT DOCUMENTS

| | | | |
|---|---|---|---|
| 3,531,300 | 9/1970 | Greenberg et al. | 426/412 |
| 3,769,028 | 10/1973 | Katz et al. | 426/412 |
| 4,667,454 | 5/1987 | McHenry et al. | 53/425 |
| 4,735,339 | 4/1988 | Benge et al. | 220/359 |
| 4,842,872 | 6/1989 | Sugisawa et al. | 426/46 |
| 4,871,565 | 10/1989 | Sugisawa et al. | 426/407 |
| 4,874,580 | 10/1989 | Sugisawa et al. | 422/25 |

FOREIGN PATENT DOCUMENTS

| | | | |
|---|---|---|---|
| 0159302 | 10/1985 | European Pat. C. | 422/25 |
| 0351599 | 1/1990 | European Pat. Off. | 99/359 |
| 2611389 | 9/1976 | Fed. Rep. of Germany | 426/232 |
| 1-302159 | 12/1989 | Japan | 426/232 |
| 0671800 | 7/1979 | U.S.S.R. | 422/25 |
| 1544260 | 4/1979 | United Kingdom | 422/25 |

OTHER PUBLICATIONS

Translation of German Patent No. 2,611,389 (Oct. 1987).
R. K. Dodrill, *Advanced Retort Systems, Inc. Introduces the Flavor Saver*, about Mar. 1990.
G. Obrecht, *Retort Data Acquisition System—Operator's Guide*, Completed on Dec. 7, 1990.
R. K. Dodrill, *Advanced Retort Systems, Inc. Presents The Solution to Optimum Autoclave Sterilization of Liquid Solutions*, Jun. 6, 1991.
R. K. Dodrill, *Advanced Retort Systems, Inc. Optimum Autoclave Sterilization of Liquid Solutions*, Mar., 1992.
R. K. Dodrill, *Rollprint Packaging Products, Inc. Optimum Autoclave Sterilization of Liquid Solutions*.
R. K. Dodrill, *Retort Sterilization—Fact vs. Myth*, Sep. 26, 1990.
Hisaka in Osaka, Japan, *The Theory of Retort Sterilization*.
R. K. Dodrill, *Advanced Retort Systems, Inc.: Hisaka Hot Water Retort Sterilizer*, Apr. 1991.

*Primary Examiner*—Robert J. Warden
*Assistant Examiner*—Laura E. Collins
*Attorney, Agent, or Firm*—McAndrews, Held & Malloy, Ltd.

[57] ABSTRACT

Sealed, deformable, air-containing packages or pouches are subject to heat sterilization in a sealable processing vessel. The shape and integrity of the sealed deformable packages is maintained through precise temperature and pressure control. The improved process includes a method for calculating the partial saturated volatile material vapor pressures during the "come-up", "processing", and "come-down" phases. The partial saturated volatile material vapor pressure used during the "come-up" and "processing" phases is calculated at the highest temperature of the contents of the package. The partial saturated volatile material vapor pressure used during the "come-down" phase is calculated at the lowest temperature of the package. The present invention discloses an improved process for controlling the pressure inside retort equipment when sterilizing food in deformable plastic packages with film-type lids and any volume of headspace. The improved process is useful for retort processes, sterilization, autoclaving and pasteurization. The improved process has food, medical and industrial applications.

25 Claims, 7 Drawing Sheets

PROCESS FOR STERILIZING THE CONTENTS OF A SEALED DEFORMABLE PACKAGE

BACKGROUND OF THE INVENTION

The present invention relates to an improved process for controlling the pressure in a processing tank or vessel used for heating and cooling deformable sealed packages having volatile contents. The invention relates more particularly to complete sterilization processes, such as retorting and autoclaving when sterilizing food, medical products or industrial products, or partial sterilization processes such as pasteurization of food or other products.

Retort sterilization of food has been an important method of food preservation for many decades. The well known process of canning is the retort sterilization of cans and jars, which are substantially non-deformable under typical retort conditions. The equipment and technology for canning is well known.

In the mid-1960's, the retort punch was commercialized in Japan for such food products as curry and stew. These pouches were essentially heavy-walled sealed plastic pouches. The retort pouch was not successful with the consuming public of the United States at that time. However, the military has used retort pouches for "MRE" or "meals ready to-eat" since the early 1970's.

The retort sterilization of food in pouches presents a significant problem for the packaging industry; namely, the pouches are prone to damage during the sterilization process. This problem is partially overcome by making the pouches stronger and more durable. Thus, one approach to retort sterilization of a pouch is to make the pouch stronger and more like a can or a jar. Of course, doing so comes at the expense of greater package cost and weight.

In the 1980's, American food companies began to investigate the use of "retortable" plastic trays, bowls, cups and other formed containers with peelable lids for shelf-stable foods. The use of plastic and other deformable food containers arose in wake of the advent of microwave ovens. Food contained in plastic retort containers can be taken off the shelf and heated in the microwave oven without the need for transferring the contents into a separate bowl or dish for heating. The popularity of these retortable plastic food containers is expected to continue its growth. However, maintaining the shape and integrity of the container and lid is essential to providing a product that is acceptable to consumers.

The problem with plastic retortable food containers is that they usually contain a certain volume of air or gas in the area above the contents, commonly referred to as headspace. When a retortable container containing food and air is heated, the air and the water vapor pressures inside the package increase. If these pressure changes are not offset properly by keeping the processing tank or vessel pressure similar to the pressure within the package, the package expands and may explode upon retorting.

Conversely, when an air-containing heated retortable container is cooled (whether after a heating step or independently), the air pressure and water vapor pressure decrease. If the pressure inside the processing tank is not reduced accordingly, the retortable container will contract and may collapse.

Thus, the retort sterilization of food in a deformable plastic container while maintaining the shape and integrity of the plastic container is a difficult task which requires precise pressure and temperature control inside the processing tank or retort chamber.

Similar problems are faced during the autoclave sterilization of medical products in deformable containers. For example, common medical applications include the sterilization of intravenous solutions, water, formulas, drugs, and liquids to be injected via syringe or other means.

Comparable problems are encountered in partial sterilization processes, and heating processes generally. The most common partial sterilization application is pasteurization. It is therefore to be understood that when the term "retort" is used, any one of the terms "pasteurize", "autoclave", or "sterilize" may be readily interchanged.

A retort or autoclave sterilization process comprises three phases: the "come-up" or heating phase, the processing (or "sterilization") phase, and the "come-down" or cooling phase.

Proper pressure control is critical to maintaining the shape and integrity of deformable packages containing headspace, especially during the "come-up" and "come-down" phases. For the purposes of the discussion below, the "gas" which fills the headspace may be nitrogen, carbon dioxide, and/or air. "Volatile material" is the water or other liquid components of the package contents which are volatile at the processing temperatures. (For most foods, the volatile material is water; however, for others it may be a mixture of components of varying volatility). For packages containing an industrial or medical devices, it may be alcohol or some other volatile material, preservative, or coating material.

The "come-up" phase is the time period in which the heating medium of the processing tank is being heated to the prescribed pasteurization or sterilization temperature. During this time, the contents of the package are also being heated and the air and water vapor pressures inside the package are increasing. The pressure inside the processing tank must be increased or the package will expand and may explode. But if the pressure in the tank is increased too much or too quickly, the package will contract and may collapse.

The processing phase is the time period in which the heating medium of the processing tank is maintained at the prescribed temperature so that the contents of the package can be sterilized. In the food industry, the degree of sterilization is described in terms of $F_o$, which represents the accumulative time in minutes that the product was exposed to thermal processing equivalent to 250° F. The $F_o$ is typically calculated at the lowest product temperature during thermal processing.

Most food retort processes use an $F_o$ significantly greater than the theoretically required value in order to assure safety. However, $F_o$ is only a theoretical standard for the sterilization of a product, and it is important to ascertain the actual level of sterilization achieved for each product using a decay test, a microbe test, or the like. In other words, the sterilization of each product should be experimentally verified before mass production of that product.

During the processing phase, the internal package or container pressure continues to increase for several minutes as the temperature of all the air and other contents of the package reach thermal equilibrium. The pressure inside the processing tank must be adjusted accordingly.

The "come-down" phase is the time period in which the heat transfer medium (usually water) and therefore the product is cooled. As the heat transfer medium is cooled, the package is cooled and the contents of the package are cooled. Consequently, the air and water vapor pressures inside the package decrease during this "come-down" phase. The pressure inside the processing tank must also be reduced or the package will contract and may collapse. However, if the tank pressure is decreased too much or too quickly, the package will expand and may explode.

Several schemes have been established to avoid the consequences of too little or too much pressure in the processing tank. Those schemes include vacuum sealing to reduce the internal air pressure; eliminating the head space in the package to an absolute minimum so as to prevent expansion of air during retorting; filling the package with heated food or contents to reduce internal pressure in the package during the processing phase; using very heavy-gauge trays and lids to withstand the pressure differential; using ultra-strong peelable seals to withstand the internal pressure in the trays; and, using lower retort temperatures and longer retort times. All of the above methods have shortcomings for the retort sterilization of a lightweight, deformable tray with a peelable lid.

Other schemes attempt to provide control over the retort vessel pressure in a manner intended to minimize the opportunity for package deformation or failure. One such scheme is the so-called "dummy method." In this scheme, a small retort chamber with a window is kept at the same temperature and pressure as the processing tank. The pressure in the processing tank is controlled on the basis of the visually observed state of deformation of the model package kept in the small chamber. It has been found, however, that a high level of skill is required for visually discerning the state of deformation of the model package in the small chamber. Furthermore, the additional small chamber requires modification of existing equipment, and a model package must be used during each sterilization cycle.

Yet another scheme is taught by Sugisawa et al., U.S. Pat. No. 4,874,580, incorporated herein by reference. Sugisawa teaches that a simple delay in the increase of pressure in the processing tank during the "come-up" phase will prevent the package from collapsing. Also, it teaches that another delay in the lowering of pressure in the processing tank during the "come-down" phase will prevent the package from exploding.

More specifically, Sugisawa teaches a two-step method. First, the pressure change pattern of the air-containing retortable package is determined by installing a thermocouple or other temperature probe inside the package. The internal package pressure is calculated according to the following equations:

$$P_c = P_a + P_w \quad (1)$$

where $P_c$ is the internal pressure of the package; $P_a$ is the partial pressure of air inside the package; and $P_w$ is the partial saturated water vapor pressure inside the package. The partial pressure of air, $P_a$, may be calculated at any air temperature using the ideal gas law as shown in Equation No. 2:

$$PV/T = \text{Constant} \quad (2)$$

where P is the absolute pressure of air or gas; V is the volume of air or gas; and T is the absolute temperature of the air or gas. Because the term PV/T of Equation No. 2 is constant, for the contents of any sealed container having initial conditions $P_1$, $V_1$, and $T_1$ and modified conditions $P_2$, $V_2$, and $T_2$, $$P_1 V_1 / T_1 = P_2 V_2 / T_2 \quad (3)$$

and, $$P_2 = P_1 V_1 T_2 / V_2 T_1 \quad (4)$$

The conditions of the package at the time it was sealed are known, and they are denoted with the subscript "p" (i.e., $P_p$, $T_p$, $P_{wp}$ etc.). Furthermore, the volume of headspace does not vary appreciably if the tank pressure and the internal container pressure are balanced; therefore the volume terms cancel. Using $P_a$ and $T_a$ as the variable pressure and temperature terms for the headspace, the gas pressure of a sealed package is expressed as:

$$P_a = P_p T_a / T_p \quad (5)$$

Substituting the terms of Equation No. 5 into Equation No. 1, $$P_c = P_p T_a / T_p + P_w \quad (6)$$

Correcting for the partial pressure contributed by any water vapor present at the time the package was sealed, Equation No. 6 becomes $$P_c = (P_p - P_{wp}) T_a / T_p + P_w \quad (7)$$

Thus, in accordance with the teachings of Sugisawa, Equation No. 7 represents the current method used to estimate the internal package pressure, $P_c$, of a sealed package during a retort or autoclaving process. However, as described below, Equation No. 7 provides only an approximation of the actual internal pressure during the retort cycle.

One general object of the invention is to provide a process for sterilizing or pasteurizing the contents of a sealed deformable package with a peelable lid, or of a peel-open pouch containing headspace, while maintaining the shape and integrity of the deformable package or pouch.

Another object of the invention is to provide an improved method for controlling the pressure inside a processing tank so that the contents inside a sealed deformable package can be sterilized or pasteurized effectively without adversely affecting the shape and integrity of the sealed deformable package and the peelable lid.

Another object of the invention is to provide an improved method for accurately calculating the partial pressure of water or volatile material vapor inside a sealed deformable package during the "come-up", processing, and "come-down" phases of a retort process.

Another object of the invention is to provide an improved method for autoclaving medical devices or industrial objects in deformable packages with peelable lids, or in peel-open pouches, while maintaining the shape and integrity of the package and lid.

Another object of the invention is to provide an improved method of pasteurizing food in sealed deformable packages with peelable lids while maintaining the shape and integrity of the package and lid.

Yet another object of the invention is to provide an improved method of autoclaving, retorting or sterilizing the contents of a sealed deformable package where a volatile material other than water is present.

Further and additional objects will appear from the description, accompanying drawings, and appended claims.

SUMMARY OF THE INVENTION

The present invention represents a major advance in the ability to accurately calculate the internal package pressure as a function of temperature, and therefore enables the operator or automatic controller to adjust the processing tank pressure to be substantially equal to the pressure within the container at any given time.

Generally speaking, to achieve the foregoing and other objects in accordance with the purposes of the present invention, as embodied and broadly claimed herein, the process for sterilizing the contents of a sealed deformable package containing air or headspace comprises heating the sealed deformable package inside a sealed processing tank. The heating medium (or water) is heated to a predetermined sterilization temperature. During this heating, or "come-up" phase, the pressure in the processing tank is maintained at a pressure equal to or about the sum of the partial pressure of air (or gas) and partial saturated water (or volatile material) vapor pressure inside the package. The partial pressure of air for all temperatures is calculated using the ideal gas law. During the "come-up" and processing phases, the partial saturated water vapor pressure is calculated at the highest temperature of the contents of the package. The highest temperature of the contents is used because it controls the rate of vaporization of water or volatile material. Typically, for a food product in a tray with a lid, the highest temperature of the contents is at the region where the contents rest against a side of the package at or just below the surface of the contents.

Use of the highest temperature of the contents for the water vapor partial pressure calculations leads to far superior and more accurate results than known before. It has been found less accurate, and consequently less effective, to use the average temperature of the contents or the temperature at the middle of the contents for calculating internal package pressure. In accordance with the present invention, it has been found that the highest temperature of the contents controls the rate of water vaporization and should be used to calculate the partial pressure of water or other volatile materials during both the "come-up" and processing phases.

After the package and its contents have reached the predetermined sterilization temperature, the pressure inside the process tank is maintained equal to about the sum of the partial pressure of air (or gas) and the partial saturated water (or volatile material) vapor pressure inside the package. The partial pressure of air is calculated using the ideal gas law at the average temperature of the headspace. During this sterilization or "processing" phase, the partial saturated water vapor pressure is again calculated at the highest temperature of the contents, and typically measured at or near the sides of the package at or just below the surface of the contents.

After the contents and the package have been maintained at the sterilization temperature for a predetermined period of time, both the contents and the package are cooled. During this "come-down" phase, the pressure inside the processing tank is maintained at about the sum of the partial pressures of the air (or gas) and the partial saturated water (or volatile material) vapor pressure inside the package. The partial pressure of air is calculated using the ideal gas law at the average temperature of the headspace. The partial saturated water vapor pressure is calculated at the lowest temperature inside the package, typically the undersurface of the lid of the package. In accordance with the present invention, the lowest temperature (at the undersurface of the lid) is used because that temperature controls the rate of condensation. The undersurface of the lid is normally the coldest part inside the package because the lid is the thinnest part of the package and therefore tends to cool faster than the remainder of the package or its contents during the "come-down" phase.

More specifically, one aspect of the invention is a process for heating the contents of a sealed deformable container having a headspace which contains a noncondensing gas, in the case where the contents of the container include a volatile material.

(In the present application, a "noncondensing gas" is a gas which will not condense to a liquid or solid under the temperature and pressure conditions which the container will experience during the process. A "volatile material" is a material which will exist as a liquid or solid material under some of the temperature and pressure conditions which the container will experience during the process, but which has an appreciable equilibrium vapor pressure under the conditions which the container will experience during the process.)

The container to be processed is sealed and placed in a processing vessel having a regulated interior pressure. When the contents of the container are heated, the current pressure inside the processing vessel is maintained at a value substantially equal to the current sum of two pressure components within the container.

("Substantially equal" pressure in the processing vessel and within the package is considered herein to have been achieved when these two pressures are maintained near enough together to prevent the container from irreversibly collapsing or expanding. The tolerable pressure difference depends on the type of package and its contents. Some pressure difference is actually desirable in some instances. For example, it is sometimes desirable to allow the package pressure to slightly exceed the processing vessel pressure to slightly inflate the package and thus prevent it from collapsing at a vulnerable point, such as a corner.)

The first component of pressure within the container is the partial pressure of the noncondensing gas inside the container at the current average temperature of the headspace of the container. This component is preferably calculate using ideal gas equations, since the noncondensing gases in the container behave as essentially ideal gases. The pressure applied by an ideal gas in a vessel of constant volume is proportional to the absolute temperature of the gas.

The other component of pressure within the container is the current partial saturated volatile material vapor pressure at the current highest temperature of the contents of the container. The volatile materials included in the containers do not behave as ideal gases because they evaporate to a substantial degree during the heating process.

Optionally, the temperature within the vessel can be maintained at a predetermined level. The vessel pressure can be maintained at the current value calculated according to the above maintaining step while the temperature is maintained at a predetermined level.

In the process just discussed, the pressure calculation can be carried out as follows. A first temperature probe is positioned to measure and communicate the current average temperature, $T_a$, in the headspace of a sealed container at any given time. A second temperature probe is positioned to measure and communicate the current highest temperature, $T_1$, of the contents of a container at any given time. Calculating means, such as a microprocessor, a programmed computer, or the like, is advantageously provided to calculate the pressure inside the container and to provide an actuating signal for a suitable means for controlling the pressure in the processing vessel.

The values of the pressure $P_p$, the saturated volatile material vapor pressure $P_{wp}$, and the temperature $T_p$ within the container at the time the container is sealed are input to the calculating means, as are the current value of $T_a$ at the first temperature probe and the current value of $T_1$ at the second temperature probe. Next, the current value of the equilibrium vapor pressure, $P_{w1}$, of the volatile material in said container is determined from the known vapor pressure of the volatile material in the container at the current value of the temperature $T_1$.

The current pressure, $P_{c1}$, inside the container is then calculated according to the equation:

$$P_{c1} = P_{w1} + (P_p - P_{wp})T_a/T_p.$$

The current pressure inside the processing vessel and outside said container is then adjusted to substantially match the current value of $P_{c1}$ within the container, as calculated above. The temperature measurement, calculation, and vessel pressure adjustment steps are repeated periodically during the process, thereby maintaining the current pressure inside the sealable processing vessel and outside the container near enough to the current value of $P_{c1}$ to prevent the container from irreversibly collapsing or expanding.

In this aspect of the invention, the step of determining for the current value of $T_1$ the corresponding current value of the equilibrium vapor pressure, $P_{w1}$, of the volatile material in the container may be carried out by using for $P_{w1}$ the value of equilibrium water vapor pressure at $T_1$ taken from a standard steam table.

Another aspect of the invention is a process for cooling the contents of a sealed deformable container having a headspace which contains a non-condensing gas, in the case where the contents of the container include a volatile material. This cooling process may be carried out after the heating process described above or independently.

To carry out this aspect of the invention, the container to be processed is sealed and placed in a processing vessel having a regulated interior pressure. When the contents of the container are cooled, the current pressure inside the processing vessel is maintained at a value substantially equal to the current sum of two pressure components within the container.

The first component of pressure within the container is the same as the first component of pressure in the heating aspect of the invention previously described. The second component of pressure within the container is the partial saturated volatile material vapor pressure at the lowest temperature inside the sealed deformable container at the given time. This lowest temperature is determined and measured much like the highest temperature of the contents of the vessel, except that the temperature probe is located in the area, typically under the lid of the container near its center, where the temperature of the interior of the container is at its lowest during a cooling cycle.

The methods of the present invention provide superior pressure and temperature control and thus a significant improvement over prior methods.

Food products, medical products, industrial devices or objects, and other products can be sterilized in deformable packages using the retort or autoclave process taught by the present invention while maintaining the shape and integrity of the packages and peelable lids.

DETAILED DESCRIPTION OF THE INVENTION

While the invention will be described in connection with certain preferred embodiments, it will be understood that the invention is not limited to those embodiments. On the contrary, the invention comprehends all alternatives, modifications, and equivalents that may be included in the spirit and scope of the invention as defined by the appended claims.

The following list of symbols will assist the reader in understanding the equations used below.

LIST OF SYMBOLS

Pressures $P_c$ = container or package internal pressure.

$P_a$ = partial pressure of air or gas inside the sealed package.

$P_p$ = container or package internal pressure at time of sealing.

$P_{wp}$ = partial saturated water or volatile material vapor pressure at the time of sealing.

$P_w$ = partial saturated water or volatile material vapor pressure during any one of the three retort phases.

$P_{w1}$ = partial saturated water or volatile material vapor pressure during the "come-up" and processing phases.

$P_{w2}$ = partial saturated water or volatile material vapor pressure during the "come-down" phase.

$P_T$ = processing tank pressure

Temperatures $T_a$ = average temperature of the air or headspace in the container.

$T_p$ = temperature of the product at the time the container was sealed.

$T_1$ = saturated water or volatile material vapor equilibrium temperature during the "come-up" and processing phases.

$T_2$ = saturated water or volatile material vapor equilibrium temperature during the "come-down" phase.

$T_{tw}$ = processing tank water (or heat transfer medium) temperature.

$T_s$ = equilibrium sterilization or processing temperature.

Other symbols $F_o$ = F-Value.

$V$ = Volume of headspace inside the container or package.

In most retort sterilizations, particularly the sterilization of food products, water is the volatile material. That being the case, the subscript "w" is used to denote the partial pressures of the volatile material. It should be noted that the present invention also applies to systems using volatile materials other than water. For example, some foods may be packed in light edible oils. For consistency, the partial pressures of the water and light oil would be denoted $P_w$ as shown above even though the "w" subscript may be misdescriptive. Also, medical devices may be sterilized in an alcohol bath. The partial pressure of alcohol would also be denoted as $P_w$. Simply put, the present invention is not limited to systems employing water as the primary volatile material.

Figure 1:
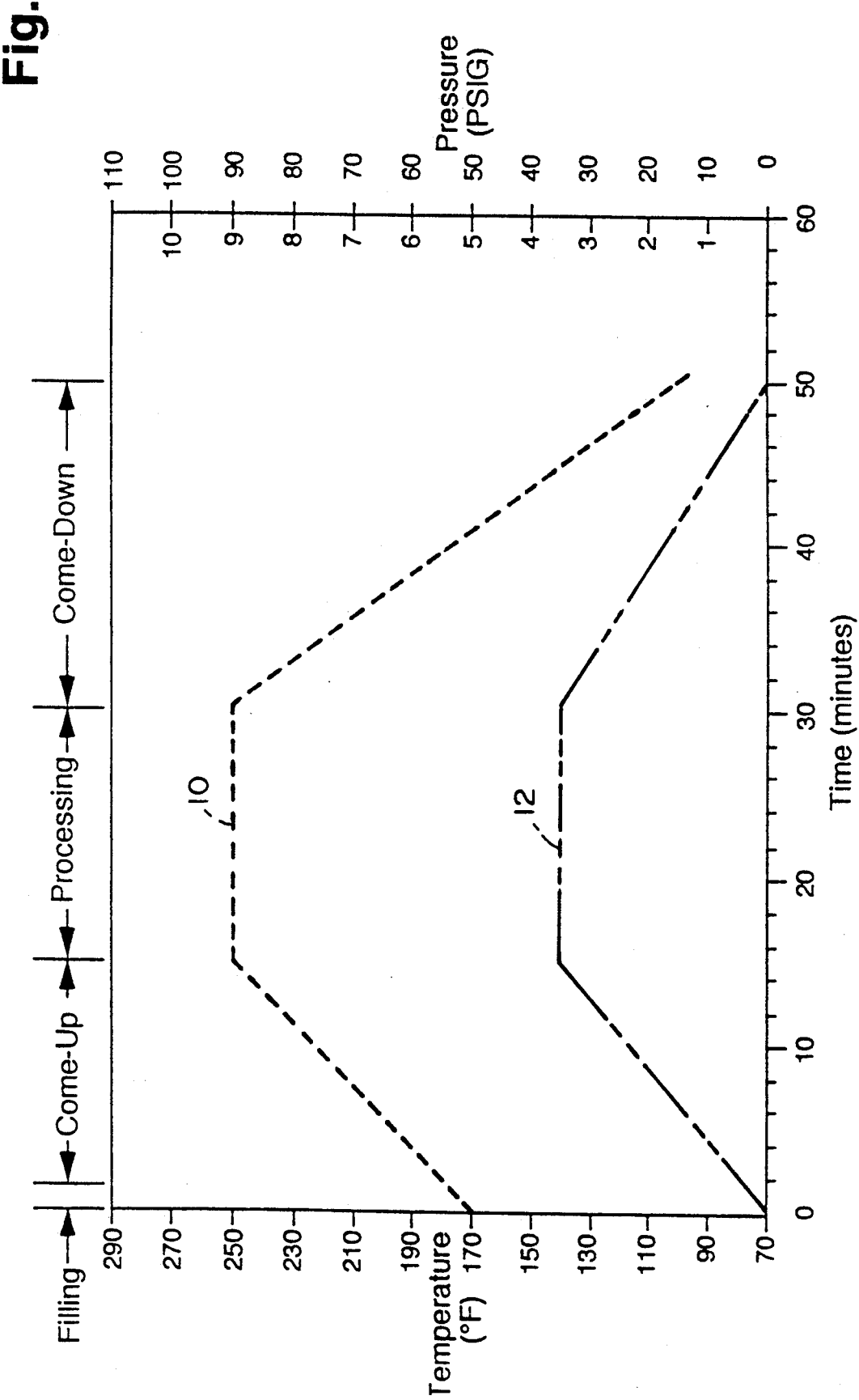
FIG. 1 is a conventional retort or autoclave pressure pattern for an air containing package, commonly referred to as the triple slope retort pattern.

Turning first to FIG. 1, a conventional retort pattern is shown for a typical food retort process. The vertical axis on the left of the figure represents the temperature of the retort water or heating medium in degrees Fahrenheit (°F.). The horizontal axis at the bottom represents the time in minutes. The vertical axis on the right hand side represents the pressure of the processing tank and internal package pressure in pounds per square inch gauge pressure, PSIG. The solid line 10 is the retort water or heating medium temperature. Starting at the left, water from a hot water reservoir is pumped or allowed to flow into the processing tank. The initial temperature of the processing water is commonly about 180° F. (about 82° C.). The entire processing tank is then heated to the sterilization temperature or processing temperature which is about 250° F. (121° C.). The initial water temperature varies depending on the nature of the process (e.g., retort or pasteurization), the type of packages and package contents and may be as low as 125° F. (52° C.) and as high as 285° F. (141° C.). The processing temperature also varies depending upon the process, product, and package.

Line 12, toward the bottom of FIG. 1, is a simplified representation of the pressure of the package and the required pressure of the processing tank. The sealed package is placed in a processing tank at about 0 PSIG (0 N/cm² gauge pressure) inside both the package and the processing tank. During the "come-up" phase, the entire processing tank is heated to the sterilization temperature and the maximum pressure. The pressure and temperature inside the package increases to about 35 PSIG (about 24 N/cm²) at 250° F. (121° C.) at thermal equilibrium. Consequently, the pressure inside the processing tank must be increased to about the same pressure or the package will expand and may explode.

The time from about 15 minutes to about 33 minutes represents the sterilization period or processing phase. In FIG. 1, during the processing phase, the retort water temperature, the processing tank pressure, and the package pressure remain substantially constant.

The downward slopes of the lines 10 and 12 on the right hand side of FIG. 1 represent the "come-down" step. At about 33 minutes on FIG. 1, the sterilization or processing step is completed and the vessel and package must be cooled. During this cooling period, the pressure inside the package decreases. The pressure in the processing tank must also be decreased or the package will be compressed and may collapse. From FIG. 1, it is evident that it is critical to control the pressure of the processing tank during the "come-up" phase on the left side of FIG. 1, the processing phase towards the center of FIG. 1 and the "come-down" phase on the right side of FIG. 1.

While FIG. 1 is a simplified representation of the temperature and pressure conditions during the "come-up" phase, processing and "come-down" phases, in reality, the temperature of the food or other contents does not respond instantaneously to the retort water temperature. Also, the temperatures and pressures inside the package do not remain constant during the early stages of the processing cycle.

Figure 2:
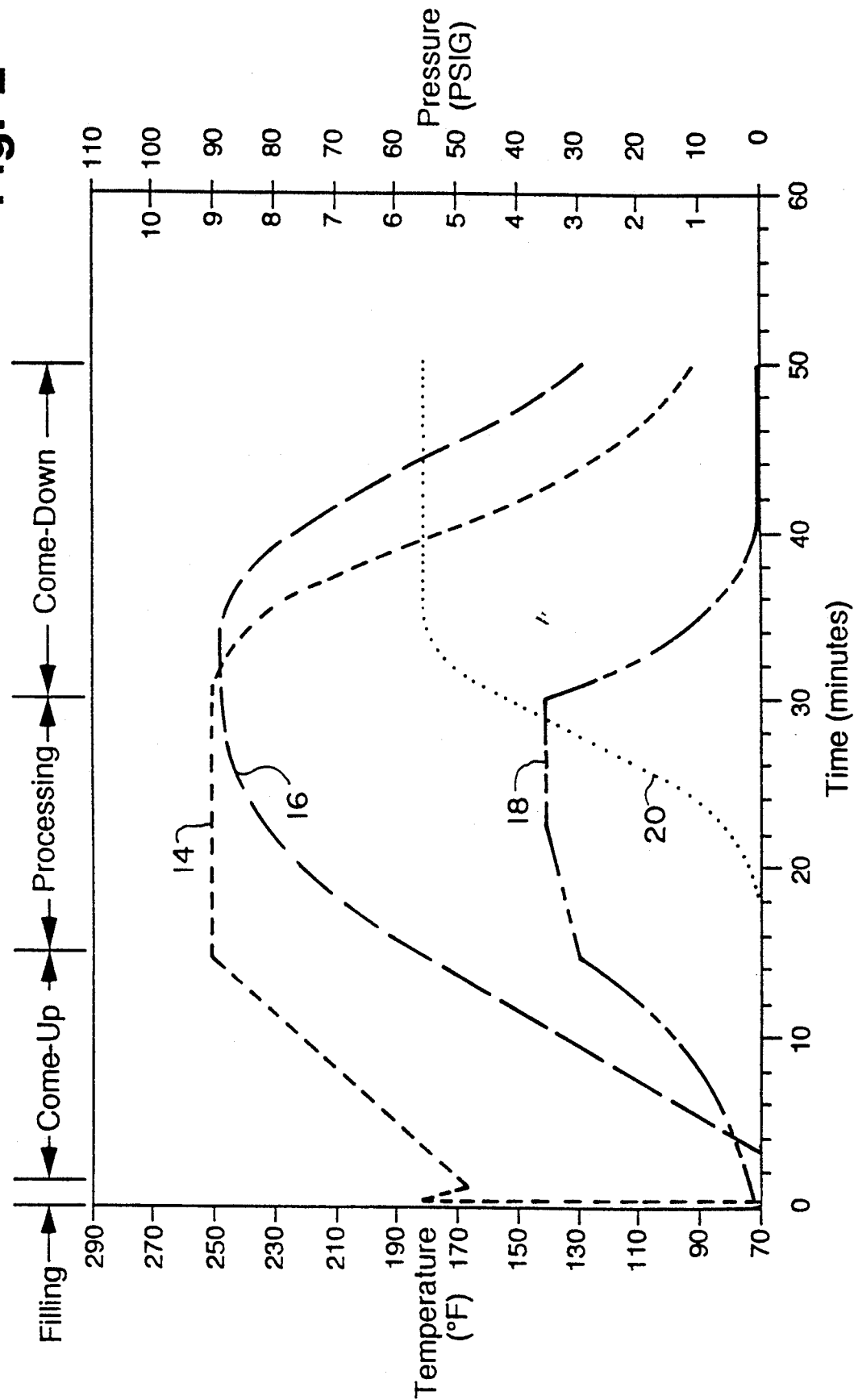
FIG. 2 is a depiction of the internal pressure in an air containing package determined in accordance with the present invention, and therefore of the pressure required in the processing tank for a retort or autoclave sterilization procedure.

These and other complications can be seen in FIG. 2. The line 14 represents the change in retort water temperature through the processing cycle. The retort water is the hot water introduced into the processing tank which provides a heat supply to heat the packages. The line 16 represents the food temperature or the temperature of the contents of the package. The temperature of the food or contents rises at a slower rate than the retort water temperature. The line 18 represents the internal pressure of the package, and consequently, the necessary internal pressure of the processing tank. The internal package pressure does not exhibit the so-called "triple slope" pattern depicted in FIG. 1. The line 20 represents the F-value or $F_o$. Because $F_o$ is a cumulative value, the curve for the F-value levels off when contents of the package begin to be cooled below the processing temperature. FIG. 2 shows an $F_o$ of 5.5 for a food retort process and the cumulative $F_o$ curve levels off at 5.5 during the "come-down" phase.

During the "come-up" phase, different foods, contents and packages will have different pressure patterns. The major factor affecting internal package pressure is the rate and extent of volatile material vaporization, and therefore, the contribution of the partial pressure of the volatile material to the total internal package pressure. For food products, the major factor for pressure control is the release of available water from the food or contents as water vapor. For the discussion below, it is assumed that the package contains food and that the volatile material is water; but, the present invention is not limited to systems where air is the headspace gas and water is the volatile material.

The internal package pressure can be calculated with knowledge of both the average air temperature in the package ($T_a$) and the saturated water vapor equilibrium temperature by use of Equation No. 7:

$$P_c = (P_p - P_{wp})T_a/T_p + P_w \quad (7)$$

Starting at the left of FIG. 2, water, at about 180° F. (82° C.), is introduced into the processing tank. The water temperature drops to 170° F. (77° C.) as the tank absorbs heat energy. The entire processing tank and the retort water are heated to about 250° F. (121° C.) For this illustrative example, this takes about fifteen minutes. During the "come-up" and processing steps, the pressure in the package increases. And, as discussed, the internal pressure of a package must be closely matched by the pressure in the processing tank. The internal package pressure inside the package can be calculated according to the following variation of Equation No. 7:

$$P_c = (P_p - P_{wp})T_a/T_p + P_{w1} \quad (8)$$

where $P_{w1}$ is the partial saturated water (or volatile material) vapor pressure calculated at the highest temperature of the contents of the package, $T_1$, or the saturated water vapor equilibrium temperature. The location within the package at which the temperature of the contents is highest is, for most food products contained in a tray having a lid, at a point approximately where the contents of the package contact a side of the package and at or just below the surface of the contents. Thus, there are two variables in the above equation, $T_a$ and $P_{w1}$.

$T_1$ is the highest temperature of the contents during the "come-up" and processing phases and is an important process parameter because, as taught here, the highest product temperature is the temperature that controls the rate of vaporization of the volatile material (or water). Existing methods rely on the use of the average temperature of the contents for $T_1$, but because the average temperature of the contents is lower than $T_1$, the value for the partial saturated water vapor pressure ($P_w$) as calculated by the existing method is too low. Recognizing this, the existing method teaches the use of a delayed value for the average temperature of the contents, or, an artificially high value for the average contents temperature. The use of the delayed (higher) contents temperature results in calculating a higher $P_w$, but is not as accurate as the method taught here. The present invention, on the other hand, provides a more accurate method of pressure control for retort sterilizations based on a better understanding of the physical phenomena involved.

As seen in FIG. 2, the temperature of the contents of the package is not constant during the "come-up" and processing phases. Therefore, the pressure inside the package is not constant during the "come-up" and processing phases. During the processing phase, the temperature of the contents approaches the prescribed sterilization temperature of 250° F. A temperature probe located in the part of the food most resistant to heating (typically the center of the product) assures that an appropriate $F_o$ is reached. (In this illustration, an $F_o$ of 5.5 is reached.)

During the "come-down" phase, the pressure inside the package is also calculated using the same equation. However, the partial saturated water vapor pressure at the equilibrium temperature is calculated at the lowest temperature inside the package, typically located at the underside of the lid of the package, because the lid is the thinnest part of the package and will respond first to the temperature of the cooling water. The lowest temperature of the air is thus used for calculating partial saturated water vapor pressure during the "come-down" phase because the lowest air temperature controls the rate of condensation. The temperature at the underside of the lid is designated as $T_2$. The equation used to calculate the internal pressure of the package during the "come-down" phase, $$P_c = (P_p - P_{wp})T_a/T_p + P_2 \quad (9)$$

has two variables: $T_a$ and $P_{w2}$. $T_a$ is the average temperature of the headspace at any given point in time. $T_a$ is measured by a probe inside the package. The second variable, $P_{w2}$, is the partial saturated water vapor pressure calculated at $T_2$, the lowest temperature inside the package (typically, the temperature of the underside of the lid). An alternative to measuring the temperature at the undersurface of the lid, $T_2$, is to employ a delay of tank water temperature, $T_{tw}$. The delay in time accounts for heat transfer through the film and the extent of the delay necessary will be dependent upon the heat transfer properties of the lid.

Standard steam tables provide a source of partial saturated water vapor pressure values and can be easily entered into the memory of a microprocessor used to control the entire process. $T_1$ for the "come-up" and processing steps can be determined during a trial run by placing a probe at the appropriate location inside the sealed deformable container. For foods contained in a tray having a lid, for example, this location is usually near the interface of the contents and a side of the tray just below the surface. During the "come-down" step, the partial saturated water vapor pressure can be taken from standard steam tables at the temperature of the undersurface or the inside surface of the lid ($T_2$). Separate probes are employed to measure $T_1$, $T_2$, $T_a$, $T_{tw}$ (for controlling the process), and the temperature at the center of the contents (for the $F_o$ determination).

By calculating the partial saturated water vapor pressures according to the two different temperature values, i.e. the values of (1) the highest temperature of the contents during the "come-up" and processing phases, which controls the rate of vaporization, and (2) the lowest temperature inside the package during the "come-down" phase, which controls the rate of condensation, one can more accurately calculate the internal pressure of the package. Consequently, by practicing the present invention, one can calculate more accurate values of the pressures required for the processing tank and thereby conduct a retort or autoclave process of a deformable package while maintaining the shape and integrity of the package and lid.

The acceptable margin of error for the processing tank pressure will depend on the type of container or package being processed and the mode of package deformation to be avoided. Generally, thicker packages and thicker lids will tolerate greater pressure differentials. For some packages, it is desirable to prevent an outward flex of the lid which will exert pressure on the lid seal and may cause the seal to leak. For these packages, the pressure in the processing tank should be kept slightly higher than the internal package pressure, $P_c$. On the other hand, some trays have a tendency to shrink or indent at processing temperatures. For these trays, it is advantageous to maintain the tank pressure below $P_c$ in order to retain the shape of the tray and package.

Figure 3:
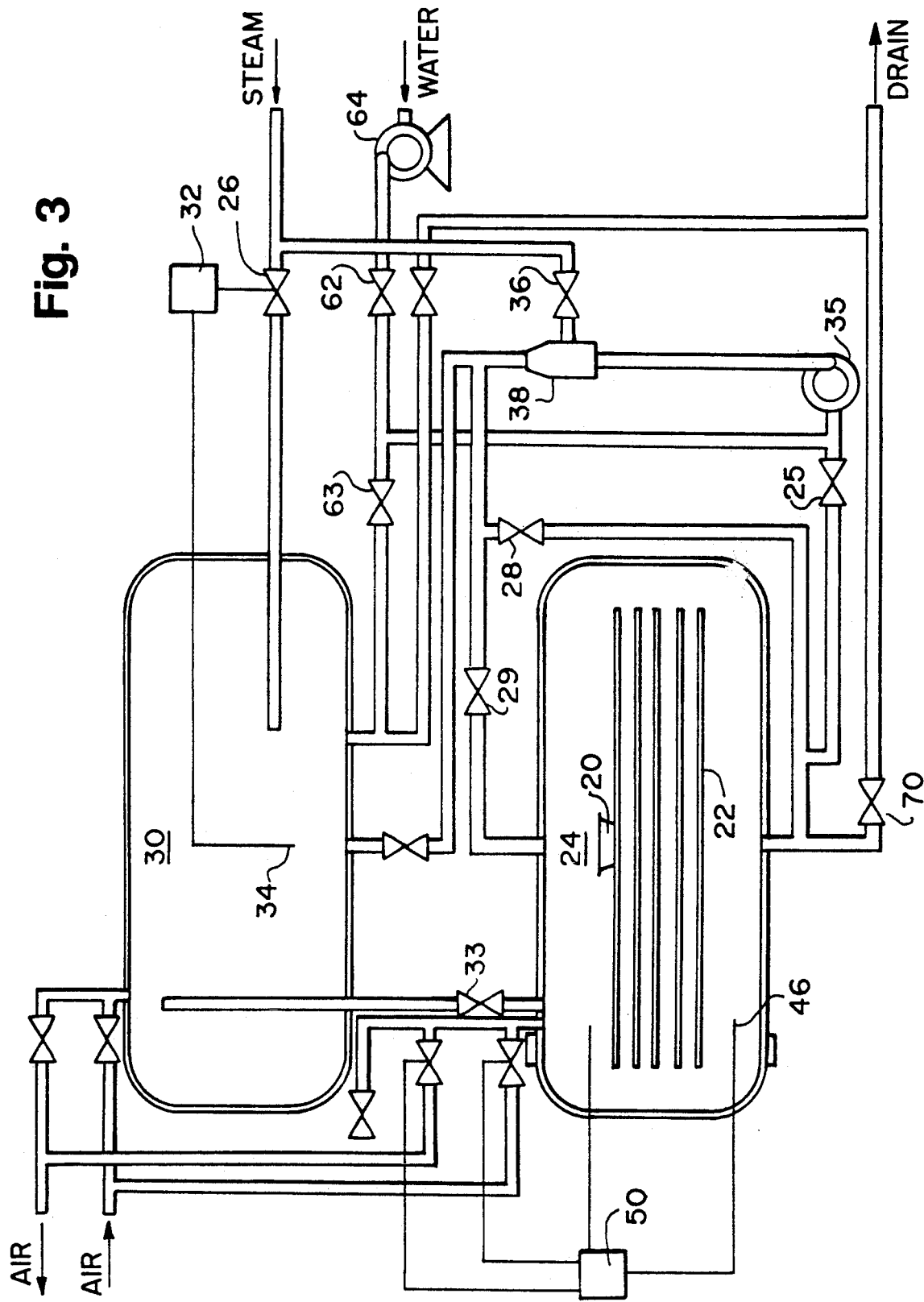
FIG. 3 is a diagram of a typical hot water immersion retort or autoclave apparatus showing the hot water tank above and the processing tank below.
Figure 4A:
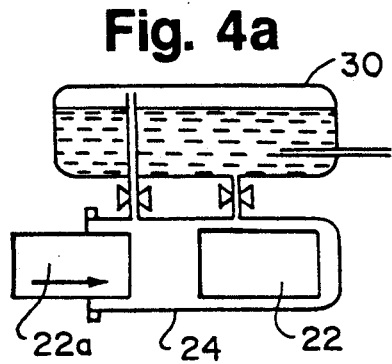
FIG. 4 is a flow diagram of a hot water immersion retort or autoclave sterilization process.
Figure 4B:
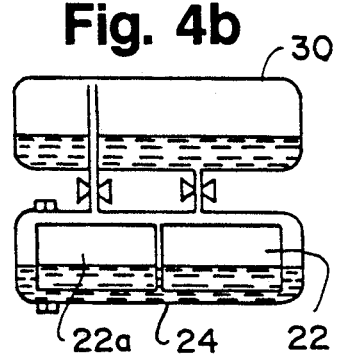
Figure 4C:
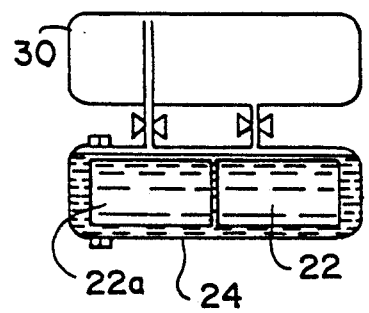
Figure 4D:
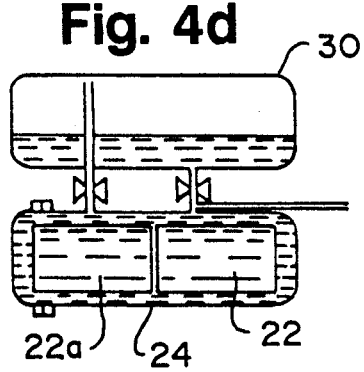
Figure 4E:
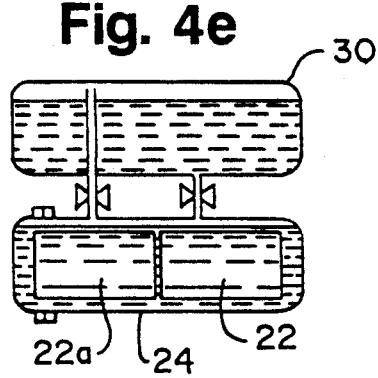
Figure 4F:
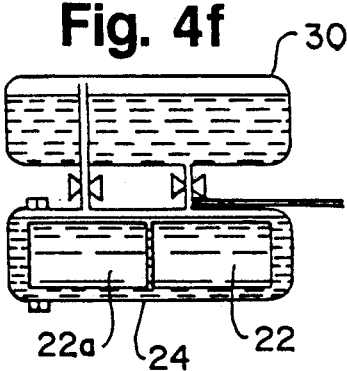
Figure 4G:
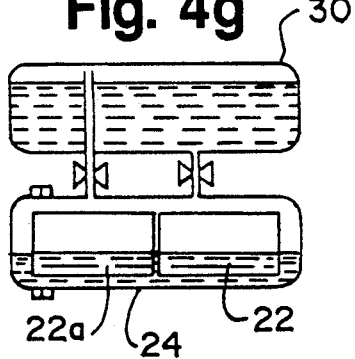
Figure 4H:
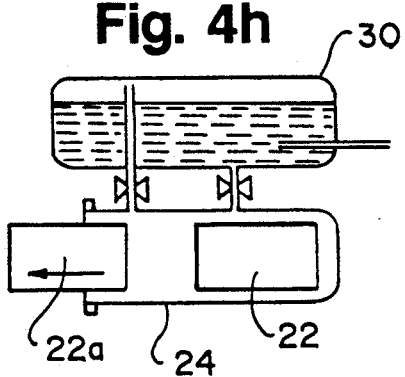
Figure 4I:
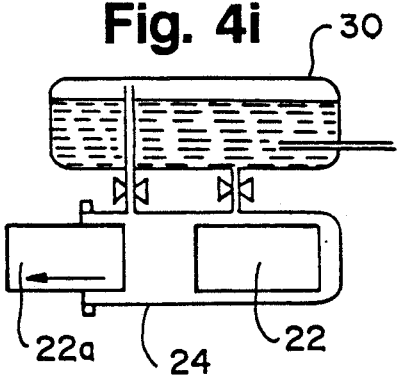

FIG. 3 is a representation of a typical apparatus used for performing a retort or autoclave process. The retort sterilization of a sealed package is carried out as follows. Air containing packages 20 are placed on the racks 22 inside the processing tank 24. The processing tank 24 is sealed. Meanwhile a valve 26 is opened allowing steam to travel into the hot water preparation tank 30. The temperature inside the hot water preparation tank 30 is controlled by a temperature controller 32 and a temperature probe 34. After the water in the hot water tank 30 reaches the desired temperature, the temperature controller 32 closes the steam valve 26. The connecting valve 33 is opened to allow pressure equalization between the two tanks. Valves 63 and 28 open and valve 29 is closed while pump 35 is activated, causing the hot water to flow from the hot water tank 30 into the processing tank 24. After the air containing packages 20 are immersed in hot water, valves 63 and 28 close. Valves 25 and 29 open to allow the hot water to be pumped through a recirculation loop. The steam valve 36 is opened to supply steam through an injector 38 into the recirculating line. At this stage, hot water in the processing tank 24 is being heated during the "come-up" phase.

After the sterilization process is completed, the steam valve 36 is closed and the injector 38 is deactivated. The hot water in the processing tank 24 is forced back into the hot water preparation tank 30 through the connecting valve 33 by cooling water being pumped through an inlet valve 62 and a supply pump 64 through a circulation pump 35. After the hot water preparation tank is filled to the appropriate level, the connecting valve 33 is closed and additional cooling water is supplied to the recirculation line. Excess processing water is eliminated through the drain valve 70. The pressure controller 50 controls the pressure inside the processing tank 24 using exhaust valve 54 and an air valve 56. Upon completion of the "come-down" phase, the cold water valve 62 is closed, and a drain 70 is opened, draining the cooling water from the processing tank.

Turning now to the flow diagram of FIG. 4, the retort sterilization process proceeds as follows:

1. The air containing packages 20 are loaded into the processing tank 24 on one or more racks schematically indicated as 22 and 22a and the water in the preparation tank 30 is heated to the specified temperature (usually 180° F. (82° C.) for food products);
2. The processing tank 24 is sealed and filled with hot water from the preparation tank 30;
3. The water in the processing tank 24 is heated to the prescribed temperature to carry out the "come-up" and processing phases;
4. Once the processing step is complete, hot water flows from the processing tank 24 back to the hot water tank 30 and the "come-down" phase is begun;
5. Cooling water is pumped into the recirculation line and into the processing tank 24 to begin final cooling;
6. The air containing packages 20 are further cooled with cooling water;
7. The cool water is discharged from the processing tank 24;
8. The air containing packages 20 are removed from the processing tank 24; and
9. The cycle is repeated for new air containing packages.

Figure 5:
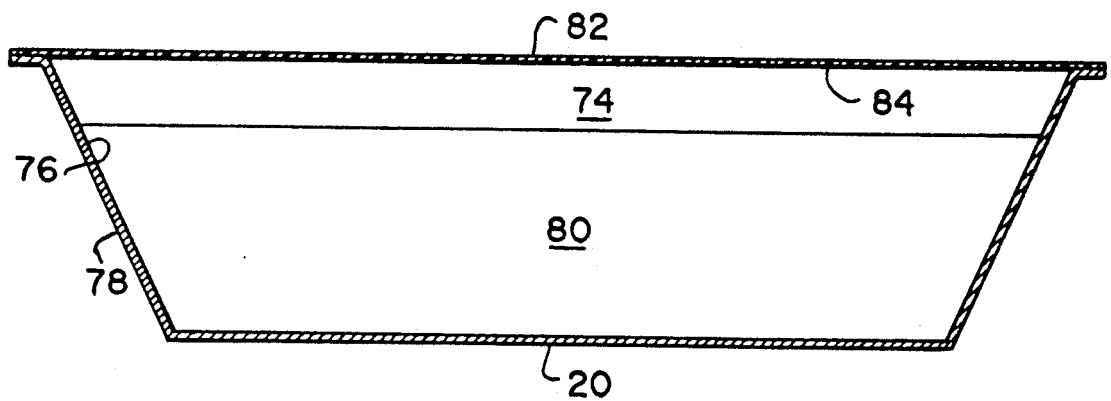
FIG. 5 is a diagram showing the location of the temperature probes during a calibration process carried out in accordance with the present invention.
Figure 6:
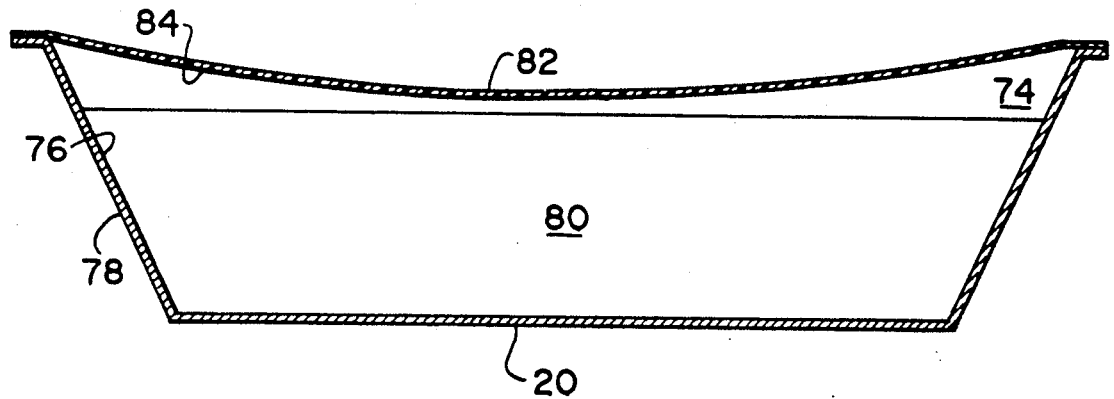
FIG. 6 is a diagram showing the location of the temperature probes during a calibration process carried out on a vacuum sealed package.
Figure 7:
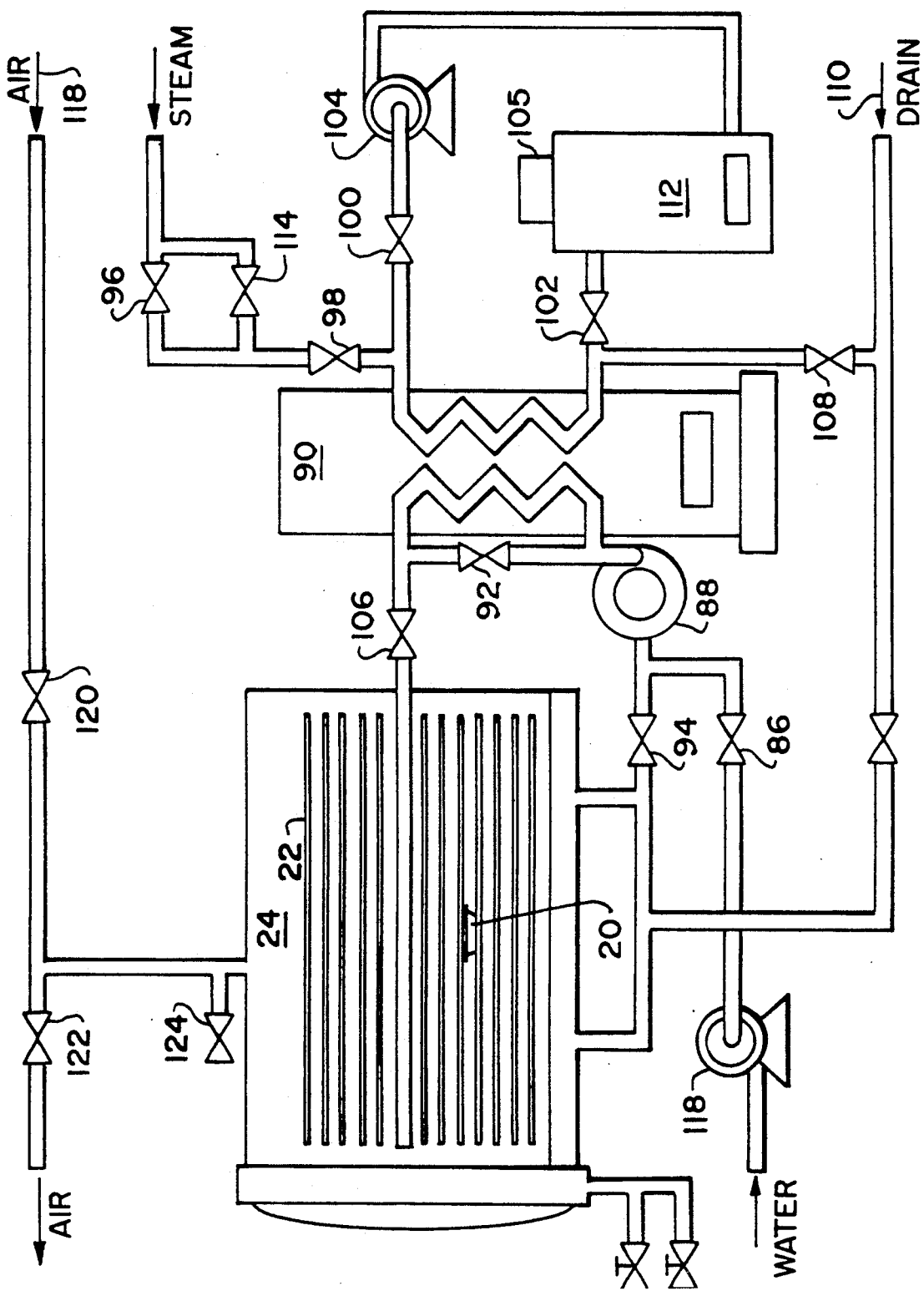
FIG. 7 is a diagram of the preferred spray retort/autoclave apparatus.

FIG. 5 is a diagram of an air containing package 20 showing the location of the four temperature probes used in the calibration process. A temperature probe 74 measures the average temperature of the air or head space of the package 20 ($T_a$). The temperature probe 76 measures the highest temperature of the contents ($T_1$), i.e., the temperature at which the saturated water vapor equilibrium pressure during the "come-up" and processing phases will be calculated. As explained above, for most foods, the temperature probe 76 should be located at the interface of the contents of the package 20 and a wall 78 of the package 20 at or just below the surface of the contents.

The temperature probe 80 measures the lowest temperature of the contents to ensure the targeted $F_o$ value is achieved. The temperature probe 80 should be located at about the center of the contents to ensure that all of the contents reach the prescribed temperature for the prescribed time period.

The temperature probe 84 measures the lowest temperature inside the package ($T_2$), i.e., the temperature at which the saturated water vapor equilibrium temperature during the "come-down" phase will be measured. For most tray and lid systems, the lowest temperature is at the underside of the lid 82. An alternative to using the probe 84 to measure the temperature at the undersurface of the lid is to use $T_{rw}$, measured by probe 46 (see FIG. 3) corrected for the time needed for heat transfer through the lid material. The extent of the delay will depend on the type of material used for the lid and the thickness of the lid.

FIG. No. 6 shows the approximate location of the probes in a vacuum sealed package. The headspace probe 74 and the $T_2$ probe 84 must be located near a side wall and away from the center of the package.

FIG. No. 7 is a schematic drawing of the preferred spray retort apparatus for carrying out the disclosed process. Rather than filling the processing tank 24 with hot water, thereby immersing the packages, hot water is sprayed over the rack 22 of packages or pouches 20.

Feed water is pumped through the feed valve 86 through the circulation pump 88 into the heat exchanger 90. At this time, the by-pass valve 92 and the stop valve 94 are closed. Heat is supplied to the heat exchanger 90 by steam that is injected through the inlet valve 96 and the steam stop valve 98. During the "come-up" phase, the cooling water inlet valve 100 and the cooling water switch valve 102 are closed. The forward pump 105 and cooling tower 112 are deactivated. Steam condensate exits the system through the steam trap 108 and the drain 110.

The feed water leaves the heat exchanger 90 through the stop valve 106 and enters the processing tank 24. The circulation pump 88 maintains sufficient pressure so that the heated feed water is sprayed over the packages in a controlled fashion.

After the processing step is completed, the feed water that is being circulated must be cooled. The steam stop valve 98 and steam inlet valve 96 are closed. The cooling water inlet valve 100 and the cooling water switch valve 102 are opened. The water feed pump 104 is activated. Cooling water circulates through the cooling tower 112 and the heat exchanger 90. The cooling water absorbs heat from the feed water, thereby lowering the feed water temperature for the "come-down" step.

The temperature during the come-up and processing steps can be controlled by regulating the supply of steam with the steam inlet valve 96, the temperature control valve 114, the steam stop valve 98 and the steam trap valve 108. The processing tank pressure is regulated with air pressure. Air pressure is provided at the air inlet 118 and controlled with the air pressure valve 120. Excess air pressure may be released through the air outlet valve 122 or the safety valve 124.

Figure 8:
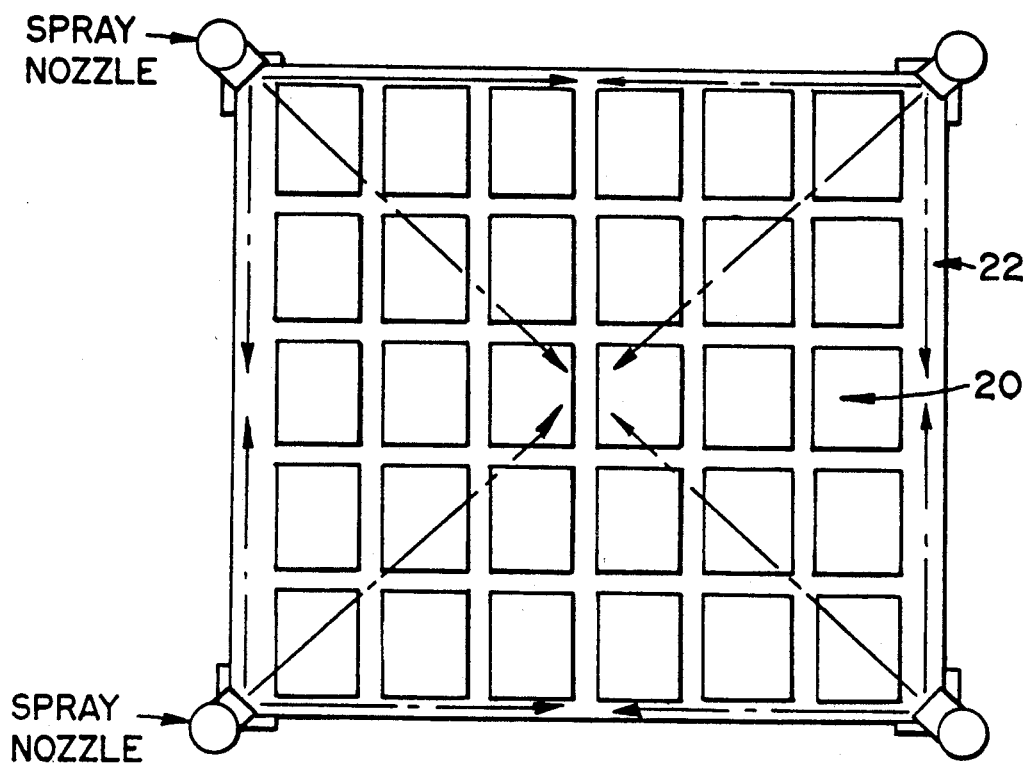
FIG. 8 is a schematic top plan view of showing the water spray pattern in the preferred spray retort/autoclave apparatus.
Figure 9:
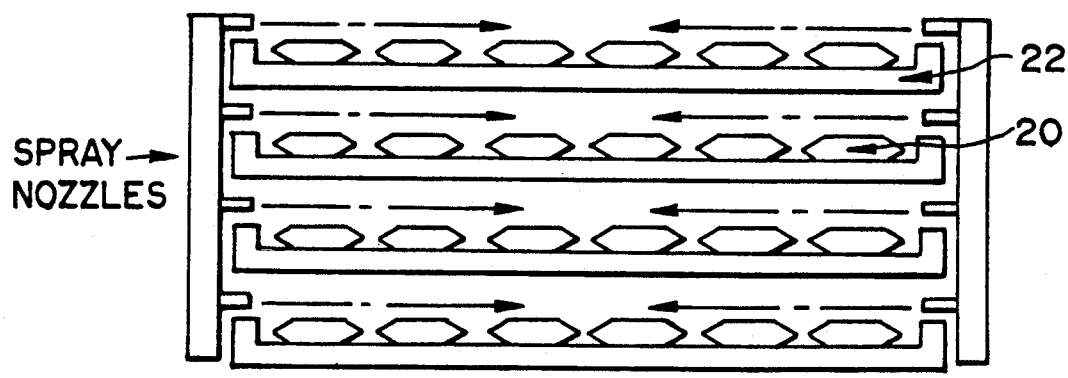
FIG. 9 is a schematic side view showing the water spray pattern in the preferred spray retort/autoclave apparatus.

FIGS. 8 and 9 show the general pattern of the hot water spray employed in the preferred apparatus. Spraying the packages with a temperature controlled water spray flow provides superior temperature control because the spray systems avoid soaking the packages in a large body of water. Water has a relatively high heat capacity and changes temperature at a slow rate. Therefore, the package temperature may be regulated faster by use of the controlled temperature spray.

During the "come-up" and processing phases, the packages are being heated. Hot water is continually sprayed on the packages and the heat-depleted water that runs off the packages is continually drained from the tank and recirculated through the heat exchanger. During the "come-down" phase, the packages are being cooled. Cold water is continually sprayed on the packages and the warmer water that runs off the packages is continually drained from the tank and recirculated and cooled through the heat exchanger. Because the spray retort system does not utilize a processing tank full of water that must be heated or cooled, the spray retort system is more economical and uniform than conventional immersion retort systems.

The present process readily lends itself to microprocessor or other computer control. A computer-controlled process may be carried out on a single retort, preferably on a sample used: (1) as a model for later commercial packages; (2) for quality control or (3) along with commercial packages for process regulation in a production run.

The "come-up" phase of the computer-controlled sterilization cycle is carried out by heating the sealed deformable container to a first predetermined temperature in the sealable processing tank, while maintaining the pressure within the deformable container and within the process tank at substantially the same values using a microprocessor or other computer control system. The pressure within the deformable container at any point during the "come-up" phase can be determined and kept substantially equal to the process tank pressure by:

A. measuring and inputting to the microprocessor the values of $P_p$ (the pressure at the time the container is sealed) and $T_p$ (the temperature of the contents of the container at the time it is sealed);

B. using a look-up table or calculation in the microprocessor based on standard steam tables, determining $P_{wp}$ (the saturated volatile material vapor pressure at the time the container is sealed), which is a function of $T_p$;

C. periodically measuring and inputting to the microprocessor the current temperature of the gas in the headspace of the container, $T_a$, measured at a first temperature probe located inside the sealed deformable container in the headspace;

D. for each input of $T_a$, calculating in the microprocessor the current partial pressure of noncondensing gas inside the sealed deformable container by solving the equation:

$$P_a = (P_p - P_{wp}) T_a / T_p;$$

E. for each input of $T_a$, measuring and inputting to the microprocessor the current highest temperature of the contents of the sealed deformable container, $T_1$, measured at a second temperature probe in the container;

F. for each input of the current value of $T_1$, using a look-up table or calculation in the microprocessor, determining the current value of $P_{w1}$ (the saturated volatile material vapor pressure during the "come-up" phase), which is a function of $T_1$;

G. for each calculated current value of $P_a$ and $P_{w1}$, calculating the current internal pressure of the sealed deformable container, $P_{c1}$, by solving the equation:

$$P_{c1} = P_a + P_{w1}; \text{ and}$$

H. regulating the current pressure inside the processing tank near enough to the current value of $P_{c1}$ to prevent the container from irreversibly collapsing or expanding.

During the processing phase of the microprocessor-controlled sterilizing cycle, the sealed deformable container is held at a predetermined temperature in the processing tank, while maintaining the pressure within the deformable container and within the process tank at substantially the same values using a microprocessor or other computer control system. The current pressure within the sealed container is calculated in the same manner as during the "come-up" phase.

The "come-down" phase of the microprocessor-controlled sterilization cycle is carried out by cooling the sealed deformable container in the sealable processing tank, while maintaining the current pressure within the deformable container and within the process tank at substantially the same values using a microprocessor or other computer control system. The current pressure within the deformable container at any point during the "come-down" phase can be determined and kept substantially equal to the process tank pressure by:

I. measuring and inputting to the microprocessor the values of $P_p$ (the pressure at the time the container is sealed) and $T_p$ (the temperature at the time the container is sealed);

J. using a look-up table or calculation in the microprocessor, determining $P_{wp}$ (the saturated volatile material vapor pressure at the time the container is sealed), which is a function of $T_p$;

K. periodically measuring and inputting to the microprocessor the current temperature of the gas in the headspace of the container, $T_a$, measured at a first temperature probe located inside the sealed deformable container in the headspace;

L. for each input of $T_a$, calculating in the microprocessor the current partial pressure of noncondensing gas inside the sealed deformable container by solving the equation:

$$P_a = (P_p - P_{wp}) T_a / T_p$$

M. for each input of $T_a$, measuring and inputting to the microprocessor the current temperature of the contents of the sealed deformable container at about the point of the lowest temperature of the contents of the sealed deformable container, $T_2$, measured at a third temperature probe in the container;

N. for each input of $T_2$, using a look-up table or calculation in the microprocessor, determining the current value of $P_{w2}$ (the saturated volatile material vapor pressure during the "come-down" phase), which is a function of $T_2$;

O. for each current value of $P_a+P_{w2}$, calculating the current internal pressure of the sealed deformable container, $P_{c2}$, by solving the equation:

$$P_{c2}=P_a+P_{w2}; \text{ and}$$

P. regulating the current pressure inside the sealable processing tank near enough to the current value of $P_{c2}$ to prevent the container from irreversibly collapsing or expanding.

A single filled and sealed deformable sample container identical to the desired production containers, but outfitted with the necessary temperature probes, can be sterilized in the production machine as a model. As the sample container is sterilized, the process water temperature in the processing tank —$T_{rw}$— and/or the elapsed time since the start of the process can be measured and inputted to the microprocessor each time the current pressure within the sealed container is calculated.

During production runs, this stored sample data correlating the elapsed time and/or process water temperature with the pressure within the sample container can be used in place of temperature probe data and ongoing pressure calculations to determine the current pressure in the production containers and to maintain the pressure within the processing tank at an appropriate value to prevent damage to the sealed containers. Using this expedient, it is not necessary to include a sample container outfitted with probes in each production run in order to acquire the data necessary to control the pressure within the processing tank accurately.

In one embodiment of the modeling process, the pressure within the sample container is determined solely as a function of the temperature ($T_{rw}$) of the process water used to heat or cool the container during a standard container processing cycle.

In another embodiment of the modeling process, the pressure within the sample container is determined solely as a function of the elapsed time since the beginning of the standard container processing cycle, then this data is used in an analogous manner during a subsequent processing cycle to determine the pressure within the container at any particular time.

EXAMPLE 1

A plastic tray with a film-type lid contains 300 cc of food and 100 cc of headspace or air. The prescribed equilibrium retort temperature is 250° F. (710° R., 121° C., 394° K.). The lid is sealed to the tray at atmospheric pressure (14.7 psia, 10.2 N/cm²) and at room temperature, 72° F. (22° C.). The partial saturated water vapor pressure (from standard steam tables) at 72° F. (22° C.) is 0.4 psig (0.28 N/cm² gauge pressure). The total package pressure at any given time can be calculated according to the following equation:

$$P_c=P_a+P_w \tag{1}$$

where $P_c$ is the pressure inside the container or sealed deformable package. $P_a$ is the partial pressure of air inside the container and $P_w$ is the partial pressure of water inside the container. $P_a$ is calculated using the ideal gas law, $PV/T=K$, where K is a constant. Therefore, $$P_1V_1/T_1=P_pV_p/T_p \tag{10}$$

whereby the subscript "p" denotes the conditions at the time the package was sealed. The conditions at the time the package was sealed are known, so $P_1$ can be determined as $$P_1=P_pV_pT_1/V_1T_p \tag{11}$$

The volume of headspace in the package is unchanged (100 cc), so the volumes cancel. Therefore, $$P_1=P_pT_1/T_p \tag{12}$$

or $$P_a=P_pT_a/T_p \tag{5}$$

where $P_a$ is the partial pressure of air; $P_p$ is the pressure at the time of sealing; $T_p$ is the temperature at the time of sealing and $T_a$ is the headspace or air temperature and varies with time. However, Equation No. 5 above does not correct for the partial saturated water vapor pressure at the time of sealing. Therefore, Equation No. 5 becomes:

$$P_a=(P_p-P_{wp})T_a/T_p \tag{13}$$

Because in this example $P_p$ is 14.7 PSIA (10.2 N/cm² absolute), $T_p$ is 72° F. (532° R., 22° C., 295° K.), and $P_{wp}$ is 0.4 PSIG (0.28 N/cm² gauge pressure), $P_a$ can be calculated according to the equation:

$$P_a 0.0269\ T_a \tag{14}$$

and $P_c$ can be calculated from equation:

$$P_c=0.0269\ T_a+P_w \tag{15}$$

where $T_a$ is the headspace temperature at any given time in degrees Rankine (°R). $P_{w1}$ is used for the "come-up" and processing cycles (Equation No. 8) and $P_{w2}$ is used for the "come-down" cycle (Equation No. 9). The saturated water vapor equilibrium temperature during the "come-up" and processing phases, $T_1$, is the highest temperature of the contents of the package because the highest temperature controls the rate of vaporization. For most foods in a tray and lid package, the highest temperature, $T_1$, is at the interface between the contents and the side of container just below the surface. The saturated water vapor equilibrium temperature during the "come-down" phase, $T_2$, is the lowest temperature of the package because the lowest temperature controls the rate of condensation. The lowest temperature, $T_2$, is at the undersurface of the lid. The total internal package pressure of an air containing tray or pouch at an equilibrium sterilization temperature, $T_s$, of 250° F. (121° C.) is 48.9 PSIA (34.2 PSIG, 34.1 N/cm² absolute, 23.8 N/cm² gauge pressure) if sealed at a packing temperature of 72° F. (22° C.) and atmospheric pressure. When both the air or headspace in the package and the highest product temperature reaches 250° F. (121° C.) during the sterilization step, the pressure in the processing tank must be equal to about 48.9 PSIA (34.2 PSIG, 34.1 N/cm² absolute pressure, 23.8 N/cm² gauge pressure) in order to maintain the shape and integrity of the package or packages.

In Example 1, the packing conditions are 72° F. (22° C., room temperature) and 14.7 PSIA (6.4 N/cm², or one atmosphere). Table 1, at the end of the specification (just before the claims), illustrates the effect of the packing conditions and processing temperatures on the internal package pressure, $P_c$.

The process disclosed by the present invention has numerous applications. It is an effective process for food pasteurization as well as food retort sterilizations, including shelf-stable food products. The disclosed process is an effective autoclaving process for medical and industrial articles and solutions, as well. The process of the invention works effectively with any deformable package including pouches and deformable trays with peelable lids. Thus, the disclosed process is effective for all sealed deformable packages containing articles or contents that require sterilization or pasteurization. The headspace gas may be air, another gas or mixture of gases. The volatile material need not be water; the disclosed process works for packages containing other volatile materials such as alcohols and oils. The processing tank employed by the disclosed process may be any sealable pressurizable vessel suited for the temperatures and pressures required.

Some food products exhibit a low water activity. The water activity of a food is defined as the ratio of the partial pressure of water vapor measured in the space over the food to the partial pressure of water vapor over pure water at the identical temperature and pressure. Foods with a water activity of less than 1.0 do not release enough water to saturate the headspace at the process temperature. For these foods, the partial pressure of water in the headspace is a fraction of that listed in standard steam tables. The actual values must be obtained through experimental analysis. However, in accordance with the present invention, the partial volatile material vapor pressures during the "come-up" and processing phases, $P_{w1}$, must be calculated at the highest temperature of the contents, $T_1$, and the partial volatile material vapor pressures during the "come-down" phase, $P_{w2}$, must be calculated at the lowest temperature of the package, $T_2$.

From the foregoing description, one skilled in the art can easily ascertain the essential characteristics of this invention, and without departing from the spirit and scope thereof, can make various changes and modifications of the invention to adapt it to various usages and conditions. These and other alternatives are considered equivalents and within the spirit and scope of the present invention.

TABLE 1

(ENGLISH UNITS)
Internal Container Pressure at Retort
Equilibrium Temperature For Various Packing
Conditions and Retort Temperatures

| $T_p$ (°F.) | $P_p$ (PSIA) | $T_s$ (°F.) | $P_a$ PSIA | $P_w$ PSIA | $P_c$ PSIA | $P_c$ PSIG |
|---|---|---|---|---|---|---|
| 50 | 14.7 | 250 | 20.2 | 29.8 | 50.0 | 35.3 |
| 50 | 14.7 | 260 | 20.5 | 35.4 | 55.9 | 41.2 |
| 50 | 14.7 | 270 | 20.8 | 41.9 | 62.7 | 48.0 |
| 50 | 12.2 | 250 | 16.7 | 29.8 | 46.5 | 31.8 |
| 50 | 12.2 | 260 | 16.9 | 35.4 | 52.3 | 37.6 |
| 50 | 12.2 | 270 | 17.2 | 41.9 | 59.1 | 44.4 |
| 50 | 9.7 | 250 | 13.2 | 29.8 | 43.0 | 28.3 |
| 50 | 9.7 | 260 | 13.4 | 35.4 | 48.8 | 34.1 |
| 50 | 9.7 | 270 | 13.6 | 41.9 | 55.5 | 40.8 |
| 72 | 14.7 | 250 | 19.1 | 29.8 | 48.9 | 34.2 |
| 72 | 14.7 | 260 | 19.4 | 35.4 | 54.8 | 40.1 |
| 72 | 14.7 | 270 | 19.6 | 41.9 | 61.5 | 46.8 |
| 72 | 12.2 | 250 | 15.7 | 29.8 | 45.5 | 30.8 |
| 72 | 12.2 | 260 | 16.0 | 35.4 | 51.4 | 36.7 |
| 72 | 12.2 | 270 | 16.2 | 41.9 | 58.1 | 43.4 |
| 72 | 9.7 | 250 | 12.4 | 29.8 | 42.2 | 27.5 |
| 72 | 9.7 | 260 | 12.6 | 35.4 | 48.0 | 33.3 |
| 72 | 9.7 | 270 | 12.8 | 41.9 | 54.7 | 40.0 |

TABLE 1-continued

| 100 | 14.7 | 250 | 17.5 | 29.8 | 47.3 | 32.6 |
|---|---|---|---|---|---|---|
| 100 | 14.7 | 260 | 17.7 | 35.4 | 53.1 | 38.4 |
| 100 | 14.7 | 270 | 18.0 | 41.9 | 59.9 | 45.2 |
| 100 | 12.2 | 250 | 14.3 | 29.8 | 44.1 | 29.4 |
| 100 | 12.2 | 260 | 14.5 | 35.4 | 49.9 | 35.2 |
| 100 | 12.2 | 270 | 14.7 | 41.9 | 56.6 | 41.9 |
| 100 | 9.7 | 250 | 11.2 | 29.8 | 41.0 | 26.3 |
| 100 | 9.7 | 260 | 11.3 | 35.4 | 46.7 | 32 |
| 100 | 9.7 | 270 | 11.5 | 41.9 | 53.4 | 38.7 |
| 150 | 14.7 | 250 | 12.8 | 29.8 | 42.6 | 27.9 |
| 150 | 14.7 | 260 | 13.0 | 35.4 | 48.4 | 33.7 |
| 150 | 14.7 | 270 | 13.2 | 41.9 | 55.1 | 40.4 |
| 150 | 12.2 | 250 | 9.9 | 29.8 | 39.7 | 25.0 |
| 150 | 12.2 | 260 | 10.0 | 35.4 | 45.4 | 30.7 |
| 150 | 12.2 | 270 | 10.2 | 41.9 | 52.1 | 37.4 |
| 150 | 9.7 | 250 | 7.0 | 29.8 | 36.8 | 22.1 |
| 150 | 9.7 | 260 | 7.1 | 35.4 | 42.5 | 27.8 |
| 150 | 9.7 | 270 | 7.2 | 41.9 | 49.1 | 34.4 |

(METRIC UNITS)

| $T_p$ (°C.) | $P_p$ N/cm² | $T_s$ (°C.) | $P_a$ N/cm² | $P_w$ N/cm² | Absolute $P_c$ N/cm² | $P_c$ N/cm² |
|---|---|---|---|---|---|---|
| 10 | 10.2 | 121 | 14.1 | 20.8 | 34.9 | 24.7 |
| 10 | 10.2 | 127 | 14.3 | 24.7 | 39.0 | 28.8 |
| 10 | 10.2 | 132 | 14.5 | 29.2 | 43.7 | 33.5 |
| 10 | 8.5 | 121 | 11.6 | 20.8 | 32.4 | 17.8 |
| 10 | 8.5 | 127 | 11.8 | 24.7 | 36.5 | 26.3 |
| 10 | 8.5 | 132 | 12.0 | 29.2 | 41.2 | 31.0 |
| 10 | 6.8 | 121 | 9.2 | 20.8 | 30.0 | 19.8 |
| 10 | 6.8 | 127 | 9.3 | 24.7 | 34.0 | 23.8 |
| 10 | 6.8 | 132 | 9.5 | 29.2 | 38.7 | 28.45 |
| 22 | 10.2 | 121 | 13.3 | 20.8 | 34.1 | 23.9 |
| 22 | 10.2 | 127 | 13.5 | 24.7 | 38.2 | 28.0 |
| 22 | 10.2 | 132 | 13.7 | 29.2 | 42.9 | 32.7 |
| 22 | 8.5 | 121 | 10.9 | 20.8 | 31.7 | 21.5 |
| 22 | 8.5 | 127 | 11.2 | 24.7 | 35.9 | 25.7 |
| 22 | 8.5 | 132 | 11.3 | 29.2 | 40.5 | 30.3 |
| 22 | 6.8 | 121 | 8.6 | 20.8 | 29.4 | 19.2 |
| 22 | 6.8 | 127 | 8.8 | 24.7 | 33.5 | 23.3 |
| 22 | 6.8 | 132 | 8.9 | 29.2 | 38.1 | 27.9 |
| 38 | 10.2 | 121 | 12.2 | 20.8 | 33.0 | 22.8 |
| 38 | 10.2 | 127 | 12.3 | 24.7 | 37.0 | 26.8 |
| 38 | 10.2 | 132 | 12.5 | 29.2 | 41.7 | 31.5 |
| 38 | 8.5 | 121 | 10.0 | 20.8 | 30.8 | 20.6 |
| 38 | 8.5 | 127 | 10.1 | 24.7 | 34.8 | 24.6 |
| 38 | 8.5 | 132 | 10.2 | 29.2 | 39.4 | 29.2 |
| 38 | 6.8 | 121 | 7.8 | 20.8 | 28.6 | 18.4 |
| 38 | 6.8 | 127 | 7.9 | 24.7 | 32.6 | 22.4 |
| 38 | 6.8 | 132 | 8.0 | 29.2 | 37.2 | 27.0 |
| 66 | 10.2 | 121 | 8.9 | 20.8 | 29.7 | 19.5 |
| 66 | 10.2 | 127 | 9.1 | 24.7 | 33.8 | 23.6 |
| 66 | 10.2 | 132 | 9.1 | 29.2 | 38.3 | 28.1 |
| 66 | 8.5 | 121 | 6.9 | 20.8 | 27.7 | 17.5 |
| 66 | 8.5 | 127 | 7.0 | 24.7 | 31.7 | 21.5 |
| 66 | 8.5 | 132 | 7.1 | 29.2 | 36.3 | 26.1 |
| 66 | 6.8 | 121 | 4.9 | 20.8 | 25.7 | 15.5 |
| 66 | 6.8 | 127 | 4.9 | 24.7 | 29.6 | 19.4 |
| 66 | 6.8 | 132 | 5.0 | 29.2 | 34.2 | 24.0 |

$T_p$ = temperature of product when package is sealed
$P_p$ = internal pressure inside package when sealed
$T_s$ = retort temperature
$P_a$ = partial pressure of air or gas inside sealed package
$P_w$ = partial saturated water/volatile material vapor pressure
$P_c$ = total pressure within package

What is claimed is:

1. A process for cooling the contents of a sealed, deformable package, comprising the steps of:

A. providing a sealed deformable container which has been sealed at a sealing temperature, $T_p$, and a sealing pressure, $P_p$, and which contains non-gaseous contents and a headspace, wherein said non-gaseous contents comprise a volatile material which has a point of lowest temperature within it and a partial saturated volatile material vapor pressure, $P_{w2}$; said headspace comprises a noncondensing gas and has an average temperature, $T_a$; and said noncondensing gas has a partial pressure, $P_a$;

B. Placing said sealed deformable container in a processing vessel including means for regulating its interior pressure, $P_T$;

C. contacting said non-gaseous contents of said sealed deformable container with a heat-transfer medium having a temperature $T_{rw}$ effective to cool said non-gaseous contents of said sealed deformable container; and D. maintaining said interior pressure $P_T$, at any given time, at a value substantially equal to the sum of
   (1) said partial pressure, $P_a$ of said noncondensing gas inside said sealed deformable container at said average temperature, $T_a$, of said headspace of said sealed deformable container at said given time, and
   (2) said partial saturated volatile material vapor pressure, $P_{w2}$, at said lowest temperature, $T_2$, inside said sealed deformable container at said given time.

2. The process of claim 1, wherein said maintaining step D is carried out by:
   A. providing a first temperature probe adapted and positioned to measure and communicate said average temperature, $T_a$, in said headspace of said sealed deformable container at any given time;
   B. providing a second temperature probe adapted and positioned to measure and communicate said lowest temperature, $T_2$, within said sealed deformable container at any given time;
   C. providing a calculator;
   D. inputting to said calculator the values of said sealing pressure $P_p$, saturated volatile material vapor pressure $P_{wp}$, and said sealing temperature $T_p$ within said sealed deformable container at the time said sealed deformable container was sealed;
   E. measuring said value of $T_a$ with said first temperature probe and said value of $T_2$ with said second temperature probe;
   F. communicating said values of $T_a$ and $T_2$ from the temperature probes to said calculator;
   G. determining for said value of $T_2$ the corresponding value of said partial saturated volatile material vapor pressure, $P_{w2}$, in said sealed deformable container;
   H. calculating the pressure $P_{c2}$, inside said sealed deformable container according to the equation:

$$P_{c2} = (P_p - P_{wp})T_a/T_p + P_{w2}$$

I. substantially conforming said pressure inside said processing vessel and outside said sealed deformable container to said value of $P_{c2}$ calculated above; and
   J. repeating said steps E, F, G, H, and I periodically during said process, thereby maintaining said interior pressure $P_T$ near enough to said value of $P_{c2}$ to prevent said sealed deformable container from irreversibly collapsing or expanding.

3. The process of claim 1, wherein said heat transfer medium is water, and wherein said maintaining step D is carried out by:
   A. providing a calculator;
   B. repeatedly measuring the temperature, $T_{rw}$, of said cooling water in said processing vessel;
   C. communicating $T_{rw}$ to said calculator; and
   D. determining for measured values of $T_{rw}$ the corresponding pressure, $P_{c2}$, within said sealed deformable container.

4. The process of claim 3, wherein said step of determining, for measured values of $T_{rw}$, said corresponding pressure, $P_{c2}$, within said sealed deformable container is carried out by:
   A. providing a sample of said sealed deformable container which is substantially identical to said sealed deformable containers to be cooled;
   B. providing a first temperature probe adapted and positioned to measure and communicate said temperature of said cooling water;
   C. providing a second temperature probe adapted and positioned to measure and communicate said lowest temperature, $T_2$, of said non-gaseous contents at any given time;
   D. providing a calculator;
   E. inputting to said calculator said values of said pressure $P_p$ and said temperature $T_p$ within said sample sealed deformable container at the time said sample sealed deformable container is sealed;
   F. placing said sample sealed deformable container in said processing vessel;
   G. cooling said non-gaseous contents of said sample sealed deformable container under the conditions intended for said process;
   H. measuring a range of representative values of $T_2$ with said second temperature probe, and measuring the corresponding values of $T_{rw}$ with said first temperature probe;
   I. determining for each of said values of $T_p$ and $T_2$ the corresponding values of $P_{wp}$ and $P_{w2}$ by finding the vapor pressure of water at $T_p$ and $T_2$ from standard steam tables; and
   J. storing in a place accessible to said calculator a database identifying said corresponding values of $T_{rw}$ and $P_{c2}$.

5. The process of claim 4, wherein said sealed deformable container has a top interior surface adjacent to said headspace, and wherein said lowest temperature of said non-gaseous contents of said sealed deformable sealed deformable container is measured within said headspace at a point on the top interior surface of said sealed deformable container.

6. A process for sterilizing contents of a sealed deformable container, comprising the steps of:
   A. providing a sealed deformable container containing non-gaseous contents and a headspace, wherein said non-gaseous contents comprise a volatile material which has a point of highest temperature and a point of lowest temperature within it and a partial saturated volatile material vapor pressure; said headspace comprises a noncondensing gas and has an average temperature, $T_a$; and said noncondensing gas has a partial pressure, $P_a$; and which container has been sealed at a sealing temperature, $T_p$ of its non-gaseous contents and a sealing pressure, $P_p$, of its headspace;
   B. determining the partial saturated volatile material vapor pressure, $P_{wp}$, of said volatile material at said sealing temperature;
   C. contacting said sealed deformable container with a first heat-transfer medium having a temperature effective to heat said non-gaseous contents of said sealed deformable container in a processing vessel;
   D. determining the partial saturated volatile material vapor pressure, $P_{w1}$, at the highest temperature of said non-gaseous contents of said sealed deformable container;

E. contemporaneously with said contacting step C, maintaining the pressure inside said processing vessel at a pressure at least about equal to the pressure, $P_{c1}$, given by the equation:

$$P_{c1} = (P_p - P_{wp})T_a/T_p + P_{w1}$$

F. maintaining said non-gaseous contents of said sealed deformable container at a temperature approaching the temperature of said first heat-transfer medium while contemporaneously maintaining the pressure inside said processing vessel at a pressure about equal to said pressure $P_{c1}$;

G. contacting said sealed deformable container with a second heat-transfer medium having a temperature effective to cool said non-gaseous contents of said sealed deformable container;

H. determining the partial saturated volatile material vapor pressure, $P_{w2}$, at the lowest temperature of said non-gaseous contents of said sealed deformable container; and I. contemporaneously with said contacting step G, maintaining the pressure inside said processing vessel at a pressure equal to about the pressure, $P_{c2}$, given by the equation:

$$P_{c2} = (P_p - P_{wp})T_a/T_p + P_{w2}.$$

7. A process for heating the contents of a sealed, deformable package, comprising the steps of:
  A. providing a sealed deformable container which contains non-gaseous contents and a headspace, wherein:
    (1) said non-gaseous contents comprise a volatile material which has a point of highest current temperature, $T_1$, within it and a current partial saturated volatile material vapor pressure, $P_{w1}$, which is a function of said highest current temperature, $T_1$;
    (2) said headspace comprises a noncondensing gas and has a current average temperature, $T_a$; and
    (3) said noncondensing gas has a current partial pressure, $P_a$, which is a function of the value of said current average temperature, $T_a$;
  B. determining the sealing temperature, $T_p$, of said non-gaseous contents and the sealing pressure, $P_p$, of said headspace when said sealed deformable container was sealed;
  C. placing said sealed deformable container in a processing vessel;
  D. contacting said sealed deformable container with a heat-transfer medium having a temperature, $T_{tw}$, effective to heat said non-gaseous contents; and
  E. maintaining current vessel pressure inside said processing vessel at a value substantially equal to the sum of
    (1) said current partial pressure, $P_a$, of said noncondensing gas at said current average temperature, $T_a$, of said headspace; and
    (2) said current partial saturated volatile material vapor pressure, $P_{w1}$, of said volatile material at said highest current temperature, $T_1$.

8. The process of claim 7, comprising the subsequent step of maintaining said non-gaseous contents at a temperature approaching said temperature of said heat transfer medium while maintaining said vessel pressure at a current value calculated according to said maintaining step E.

9. The process of claim 7, wherein said non-gaseous contents have an interface with said headspace defining a surface, said sealed deformable container comprises a wall touching said non-gaseous contents adjacent to said surface, and said highest current temperature of said non-gaseous contents is measured at a point where said non-gaseous contents contact said wall of said sealed deformable container, below and proximate to said surface.

10. The process of claim 7, wherein said sealed deformable container is a pouch.

11. The process of claim 7, wherein said sealed deformable container is a peelable lid.

12. The process of claim 7, wherein said sealed deformable container is a weld seal.

13. The process of claim 7, wherein said current partial pressure, $P_a$, of said noncondensing gas inside said sealed deformable container is calculated by:
  A. determining said current average temperature of said headspace, $T_a$; and
  B. solving the equation:

$$P_a = P_p (T_a/T_p).$$

14. The process of claim 7, wherein said current partial pressure, $P_a$, of said noncondensing gas is corrected by determining partial saturated volatile material vapor pressure, $P_{wp}$, of said non-gaseous contents at said sealing temperature and subtracting said partial saturated volatile material vapor pressure, $P_{wp}$, from said current partial pressure, $P_a$, of said noncondensing gas.

15. The process of claim 7, wherein said non-gaseous contents are food products.

16. The process of claim 7, wherein said non-gaseous contents are medical products.

17. The process of claim 7, wherein said non-gaseous contents are industrial products.

18. The process of claim 7, wherein said noncondensing gas is air.

19. The process of claim 7, wherein said volatile material is water.

20. The process of claim 7, wherein said maintaining step E is carried out by:
  A. providing a first temperature probe adapted and positioned to measure and communicate said current average temperature, $T_a$, in said headspace of said sealed deformable container;
  B. providing a second temperature probe adapted and positioned to measure and communicate said highest current temperature, $T_1$, of said non-gaseous contents of said sealed deformable container;
  C. providing a calculator;
  D. determining partial saturated volatile material vapor pressure $P_{wp}$ of said non-gaseous contents at said sealing temperature, $T_p$;
  E. inputting to said calculator the values of said sealing pressure $P_p$, said partial saturated volatile material vapor pressure $P_{wp}$, and said sealing temperature $T_p$ within said sealed deformable container, each determined as of the time said sealed deformable container is sealed;
  F. measuring $T_a$ with said first temperature probe and $T_1$ with said second temperature probe;
  G. communicating current values of $T_a$ and $T_1$ from said temperature probes to said calculator;
  H. determining said current value of $T_1$ and the corresponding current value of the equilibrium vapor pressure, $P_{w1}$, of said volatile material in said sealed deformable container;

I. calculating the current pressure, $P_{c1}$, inside said sealed deformable container according to the equation:

$$P_{c1} = P_{w1} + (P_p - P_{wp})T_a/T_p;$$

J. substantially conforming said current pressure inside said processing vessel to said current value of $P_{c1}$ calculated above; and K. repeating said steps E, F, G, H, and I periodically during said process, thereby maintaining said current pressure inside said processing vessel near enough to said current value of $P_{c1}$ to prevent said sealed deformable container from irreversibly collapsing or expanding.

21. The process of claim 20, wherein said step of determining the current value of said equilibrium vapor pressure $P_{w1}$ corresponding to said current value of $T_1$ is carried out by finding the vapor pressure of water at $T_1$ from standard steam pressure tables.

22. The process of claim 7, wherein said processing vessel increases said temperature of said sealed deformable container by contacting said sealed deformable container with heated water within said processing vessel, and wherein said maintaining step E includes the steps of:
   A. providing a calculator;
   B. repeatedly measuring said temperature, $T_{tw}$, of said heated water in said processing vessel;
   C. communicating $T_{tw}$ to said calculator; and
   D. determining for said temperature, $T_{tw}$, the corresponding current total pressure within said sealed deformable container.

23. The process of claim 22, wherein said step of determining for said current value of $T_{tw}$ the corresponding current total pressure within said sealed deformable container is carried out by:
   A. providing a sealed deformable sample container which is substantially identical to said sealed deformable containers to be heated, wherein said sealed deformable sample container contains non-gaseous contents and a headspace, wherein said non-gaseous contents of said sealed deformable sample container comprise a volatile material which has a highest temperature at some point within it and a partial saturated volatile material vapor pressure, $P_{w1}$; said headspace of said sealed deformable sample container comprises a noncondensing gas and has an average temperature, $T_a$; and said noncondensing gas has a partial pressure, $P_a$;
   B. providing a temperature probe adapted and positioned to measure and communicate said current value of $T_{tw}$ and means for determining said pressure within said sample sealed deformable container, $P_c$;
   C. placing said sample sealed deformable container in said processing vessel;
   D. contacting said sample sealed deformable container with a heat-transfer medium having a temperature effective to heat said non-gaseous contents of said sealed deformable container under the conditions intended for the process;
   E. communicating said corresponding values of $T_{tw}$ and said pressure $P_c$ within said sample sealed deformable container to said calculator; and
   F. storing in a place accessible to said calculator a database identifying the corresponding values of $T_{tw}$ and said pressure, $P_c$, within said sample sealed deformable container at each given time during the execution of said process.

24. The process of claim 7, wherein said maintaining step E includes the steps of:
   A. providing a calculator;
   B. repeatedly measuring the time elapsed since the beginning of said contacting step; and
   C. determining for said current value of said elapsed time said corresponding current total pressure within said sealed deformable container.

25. The process of claim 24, wherein said step of determining, for said current value of said elapsed time, said corresponding current pressure within said sealed deformable container is carried out by:
   A. providing a sample of said sealed deformable container which is substantially identical to said sealed deformable containers to be heated, and which is packed at a known temperature and pressure, wherein said sealed deformable sample container contains non-gaseous contents and a headspace, wherein said non-gaseous contents comprise a volatile material which has a highest temperature within it and a partial saturated volatile material vapor pressure, $P_{w1}$; said headspace comprises a noncondensing gas and has an average temperature, $T_a$; and said noncondensing gas has a partial pressure, $P_a$;
   B. providing means for measuring said average temperature, $T_a$, of said headspace and said highest temperature of said non-gaseous contents within said sample sealed deformable container;
   C. providing a calculator;
   D. placing said sample sealed deformable container in said processing vessel;
   E. contacting said sample sealed deformable container with a heat-transfer medium under conditions intended to be used to heat said sealed deformable containers;
   F. determining the corresponding values of said elapsed time and the pressure within said sample sealed deformable container, wherein said pressure is calculated from said temperatures and pressures identified in steps A and B above and standard steam tables; and
   G. storing in said calculator a database identifying the value of said pressure within said sealed deformable container at each given time during the execution of said process.

* * * * *